United States Patent [19]

Skala et al.

[11] Patent Number: 4,836,029
[45] Date of Patent: Jun. 6, 1989

[54] METHOD AND APPARATUS FOR MEASURING CRACK GROWTH

[75] Inventors: Dennis P. Skala, Fairview; John W. Kloss, North East, both of Pa.

[73] Assignee: Lord Corporation, Erie, Pa.

[21] Appl. No.: 173,341

[22] Filed: Mar. 25, 1988

[51] Int. Cl.$^4$ .......................................... G01N 19/08
[52] U.S. Cl. ...................................... 73/799; 73/810
[58] Field of Search ...................... 73/799, 810, 835; 364/508

[56] References Cited

U.S. PATENT DOCUMENTS

| | | |
|---|---|---|
| 3,087,148 | 4/1963 | Ludewig, Jr. . |
| 3,803,906 | 4/1974 | Ross . |
| 3,908,447 | 9/1975 | Salt . |
| 3,983,745 | 10/1976 | Juusola . |
| 4,003,246 | 1/1977 | Caln . |
| 4,574,642 | 3/1986 | Fleischman ........................... 73/799 |

FOREIGN PATENT DOCUMENTS 587362  1/1978  U.S.S.R. ............................... 73/799

Primary Examiner—Jerry W. Myracle
Attorney, Agent, or Firm—Philip P. McCann; James W. Wright

[57] ABSTRACT

A method and apparatus for determining crack growth in an elastomer. A horizontally elongate elastomeric test specimen is cyclically stretched crosswise by upper and lower rigid plates contiguously attached to the long edges on both sides. The lengthwise growth of a crack induced by a small cut at one vertical edge of the specimen is determined by measuring the stretching force at each end. The lower plate is reciprocated by a hydraulic actuator relative to the upper plate. Two load cells measure the forces at each end of the specimen. With the use of a computer program and the relative forces measured by the load cells, the crack growth can be calculated.

17 Claims, 5 Drawing Sheets

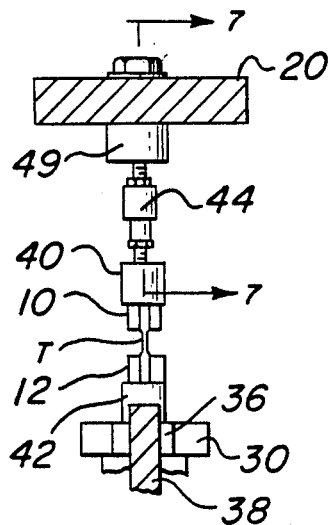
FIG. 6
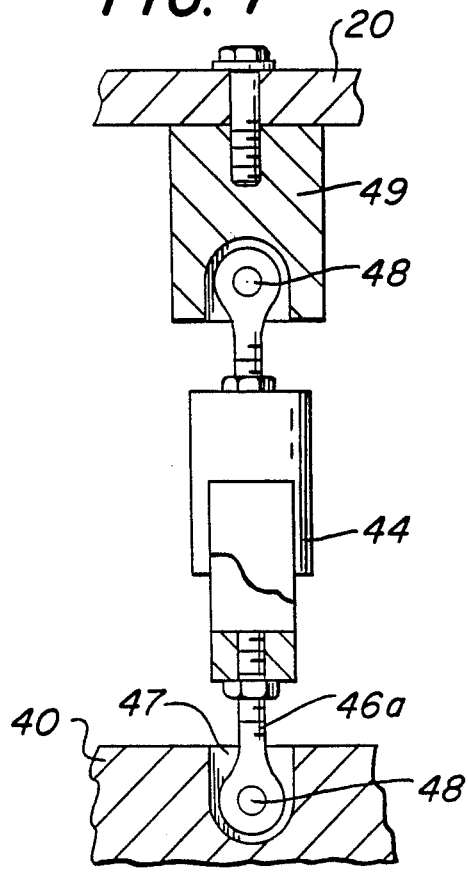
FIG. 7
FIG. 3

METHOD AND APPARATUS FOR MEASURING CRACK GROWTH

FIELD OF THE INVENTION

The present invention relates to materials testing, and more particularly to method and apparatus for determining crack growth in elastomeric test specimens.

DESCRIPTION OF THE PRIOR ART

Crack propagation, or growth, is one manifestation of structural fatigue and fracture in materials and is an important consideration in determining the useful life of a product. Materials which are subjected to repeated stress are particularly vulnerable to such growth. Various techniques for measuring crack growth are well known in the art. For example, a displacement gauge or extensometer may be attached to a test specimen for measuring the opening across a crack and correlating it with other parameters to determine the crack length. Foil gauges can also be utilized which, when bonded to the surface of the specimen in front of the path of an advancing crack, sense passage of the crack by changes in electrical resistance. These devices are used mostly in testing relatively high modulus materials. For soft materials, such as elastomers, visual techniques are generally used. Most commonly, the length of the crack is periodically measured optically with a microscope, cathetometer, or similar precision instrument.

These and other prior art techniques are usually accomplished manually, or automatically with relatively sophisticated instrumentation.

OBJECTS OF THE INVENTION

With the foregoing in mind, an object of the present invention is to provide an improved testing method and apparatus which subjects a test specimen to pure shear strain and which acquires from the dynamic force data, information necessary to determine crack growth.

Another object is to provide a novel method and apparatus which can be operated automatically with increased accuracy and efficiency for maximum testing machine utilization and data reduction.

Another object is to provide a testing apparatus which is relatively simple to operate and maintain, which is inexpensive to manufacture and can be constructed from standard, commercially available materials and components.

A further object is to provide apparatus which is particularly suited for evaluating elastomeric materials.

SUMMARY OF THE INVENTION

More specifically, the method of the invention is accomplished by inducing a crack at one vertical end of a horizontally elongate test specimen and cyclically stretching the specimen crosswise between two rigid test fixtures which are contiguously attached to the opposite long edges of the specimen. The stretching force at each end of the specimen is measured and used along with the length of the specimen for determining the lengthwise crack size. A novel testing machine for carrying out the method includes means for securing one of the test fixtures to a stationary crosshead which, in turn, is connected to a frame through two load cells aligned with the ends of the specimen. The other test fixture is secured to a movable crosshead and actuator for cyclically stretching the specimen. Eight wire braces restrain unwanted movement of the fixtures. With the use of a computer program and the relative forces measured by the load cells, the crack growth rate can be calculated.

BRIEF DESCRIPTION OF THE DRAWINGS

The foregoing and other objects, advantages and features of the present invention should become apparent from the following description of the invention when taken in conjunction with the accompanying drawings, in which:

FIG. 3 is a simplified schematic diagram of the test specimen of FIG. 2 under stress with crack growth present;

FIG. 6 is a side view of the testing machine at the specimen taken in cross section along the line 6—6 of FIG. 1;

FIG. 7 is a cross sectional view of a portion of the testing machine taken along the line 7—7 of FIG. 6;

DESCRIPTION OF THE PREFERRED EMBODIMENT

Figure 1:
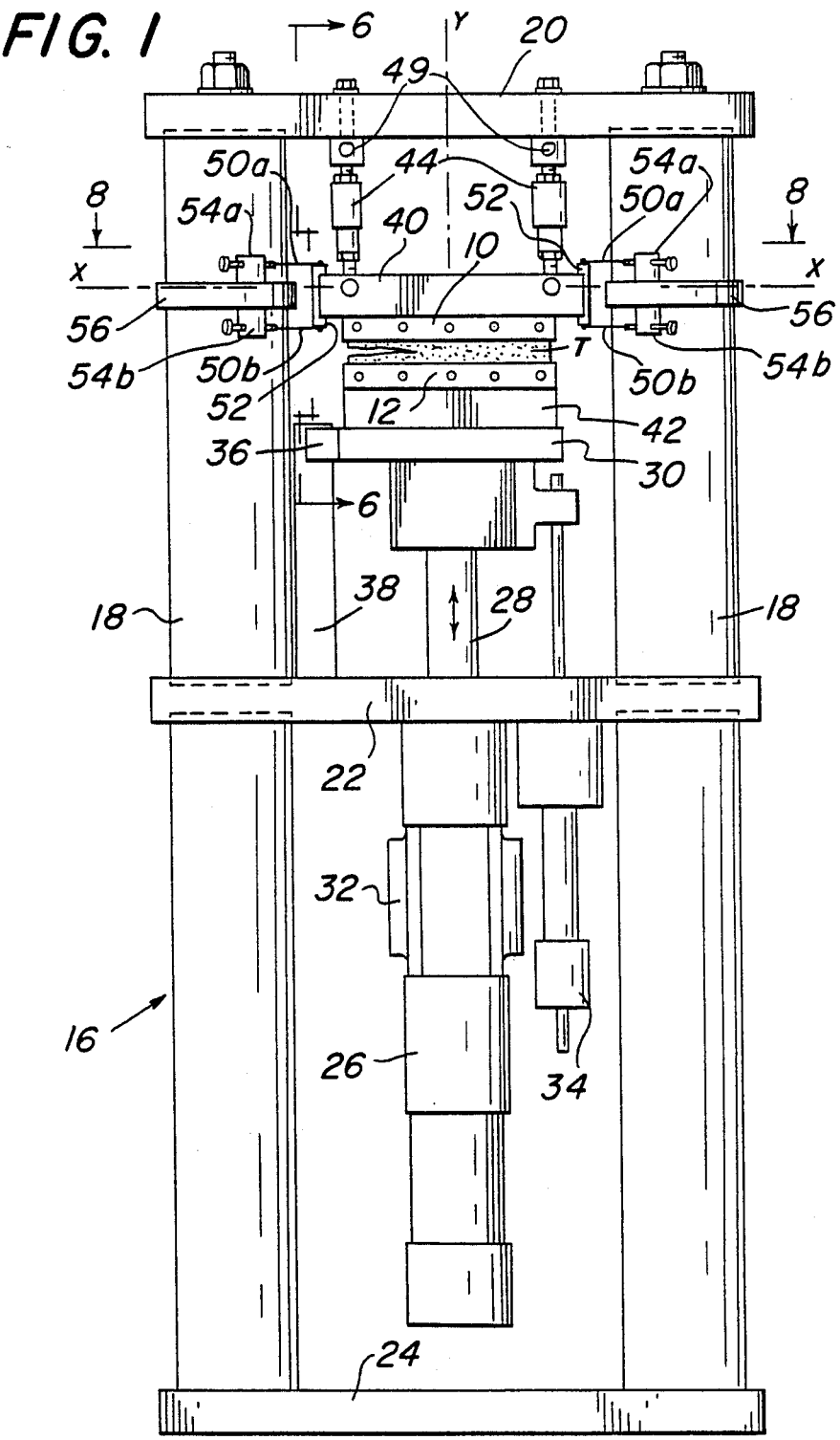
FIG. 1 is a front view, in elevation, of a testing machine embodying the invention, with the specimen of FIG. 1 mounted for testing therein.

Referring now to the drawings, FIG. 1 illustrates a testing machine 16 with an elastomeric test specimen T being stretched in pure shear with a crack propagating from the left side.

Shear is defined as deformation in which one of the three principle strains is zero. It can be achieved in several ways in elastomers. One simple way involves bonding the elastomer between two parallel flat fixtures, the fixture dimensions in length being much greater than the elastomer wall thickness. One of the fixtures is then translated relative to the other with the wall thickness remaining constant. Another method, which is utilized in the present invention, applies tension in the widthwise direction of a elongate specimen. The elastomer decreases in thickness as it increases in width, but it does not change appreciably in length. Hence, an element near the longitudinal centerline of the elastomer is in pure shear; that is, the principle strain, parallel to the length of the specimen, is zero. This particular state of strain in the sample is "pure" because the principle axes of strain do not change direction with increasing strain, as would happen with simple shear.

The dimensions of test specimen T, unstressed, are selected to have desirable ratios of length-to-width and width-to-thickness. In the ideal case, the ratios should be as large as possible, but from a practical standpoint, the specimen must be of a moderate size. Therefore, ratios of 10 were selected resulting in a molded sample 5.00 inches long (L), 0.50 inches wide ($h_o$) and 0.05 inches thick ($t_o$).

Figure 2:
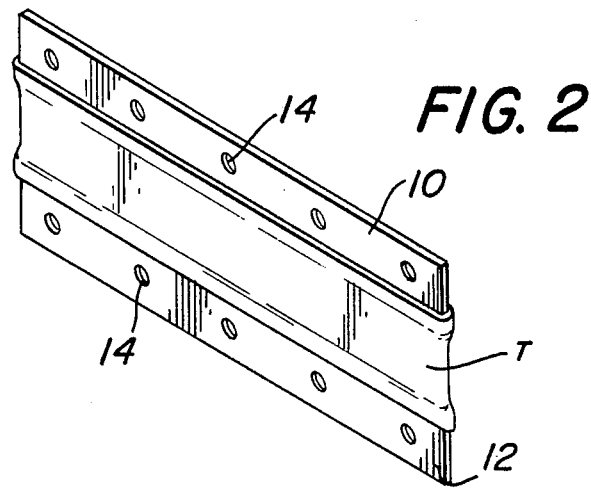
FIG. 2 is an isometric view of a test specimen prepared for mounting in the testing machine of FIG. 1.

Referring to FIG. 2, specimen T is contiguously bonded along both sides of the longitudinal edges to opposed pairs of upper and lower fixtures 10 and 12 respectively, with a plurality of aligned holes 14 through plates 10 and 12 at spaced intervals along their lengths.

Figure 4:
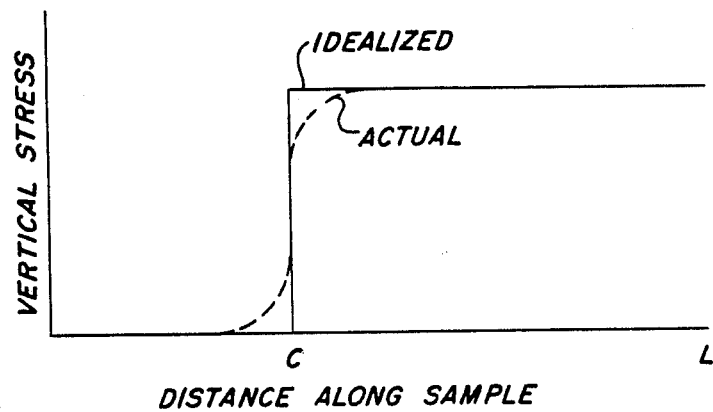
FIG. 4 is a stress distribution graph for the test specimen of FIG. 3.

The present invention has its greatest utility in the measurement of crack length and crack growth in relatively wide test samples which are commonly used in fatigue-fracture evaluation of elastomers. Referring to the schematic diagram in FIG. 3, the driving force for crack growth (tearing energy) is straightforward to measure and calculate. To a first approximation, when a force F is applied across the cracked speciment T, the elastomeric material above and below the crack line becomes stressed uniformly, i.e. the top and bottom surfaces are constrained to remain straight, unstretched in their own planes, and parallel to each other. This idealized stress distribution is shown in FIG. 4. Also shown is a typical, actual stress distribution as calculated by a plane stress finite element method. With the proper choice of specimen geometry, the idealized distribution is a good approximation of the real situation. For instance, where the unstressed specimen length-to-width ratio $L/h_o=10$, the transition from zero to full stress occurs over a distance of 0.16 x L for overall extension up to 100%. The free edges of specimen T (left and right edges in FIG. 3) thus have a neglible effect on the stress distribution so long as the crack-to-length ratio c/L is greater than 0.08 and less than 0.92. As the crack grows, the stress distribution remains unchanged in shape and simply propagates along the specimen T as the crack grows.

The length of the crack at any instant is, therefore, determined from the magnitude and position of the forces applied to specimen T. The downward force F applied to lower fixture 12 and reaction forces $F_1$ and $F_2$ at the ends of specimen T will enable a determination of the length of the crack. Assuming that the vector force F always passes through the center of the uncracked portion of specimen T, the length c of the crack can be determined. Taking moments about the force F:

$$F_1\left(\frac{L+c}{2}\right) = F_2\left(\frac{L-c}{2}\right) \quad (1)$$

and solving equation (1) for c, $$c = \frac{F_2 - F_1}{F_2 + F_1} L \quad (2)$$

The accuracy of the above calcuation depends on the exact geometry of the test specimen. For a specimen with actual measurements of $L=5.0$ inches, $h_o=0.5$ inches and a crack $c=1.0$ inches, equation (2) was applied to finite element results for an overall extension of 100%. The calculated value c was 0.9 inch which is considered a fair approximation to the real value of $c=1.0$ inches. Although this kind of accuracy may not be sufficient for some purposes, the error is independent of the crack length over the range of crack lengths in which the free edges do not effect the stress distribution. This observation is extrapolated to produce accurate calculations of crack growth and growth rate, since the constant error in calculated crack length will cancel when two subsequent calculated lengths are subtracted. Crack growth and growth rate are typically of more significance and utility than the absolute crack size.

It is important to note that the crack growth determination is predicated upon the crack propagating from only one end of the specimen. This is ensured by initiating the first failure with a small cut at one vertical end edge with a sharp blade; the other end of the specimen must remain intact. The depth of the cut should be only sufficient to ensure further cracking without further intervention. The crack propagation must also be "well-behaved" by staying reasonably close to the longitudinal center of the specimen, as is usually the case. Since the method of calculating the crack length is valid only if there is one failure, other spontaneous failures must not occur.

Referring again to FIG. 1, test specimen T is secured in a testing machine 16 for cyclical stretching and measuring the forces $F_1$ and $F_2$. The machine 16 includes upper and lower horizontal beams 20 and 22 and a base 24 separated by two columns 18 fixed in parallel and spaced relation. A reciprocating hydraulic actuator 26, between the columns 18, is attached to and extends downwardly from the lower beam 22. A rod 28 extending up through the lower beam 22 is reciprocated by the actuator 26 to provide vertical motion to a platform 30 fixed to the end of the rod 28. A conventional closed-loop, hydraulic servo system including a servo valve 32 and a platform motion sensor 34 regulates the desired amplitude and frequency of the motion to be imparted by the actuator 26. The platform 30 is prevented from rotation about its vertical axis by a bifurcated arm 36 extending from the platform 30 and slideably engaging a vertical track 38 which is rigidly fixed to and extends up from the lower beam 22.

Figure 5:
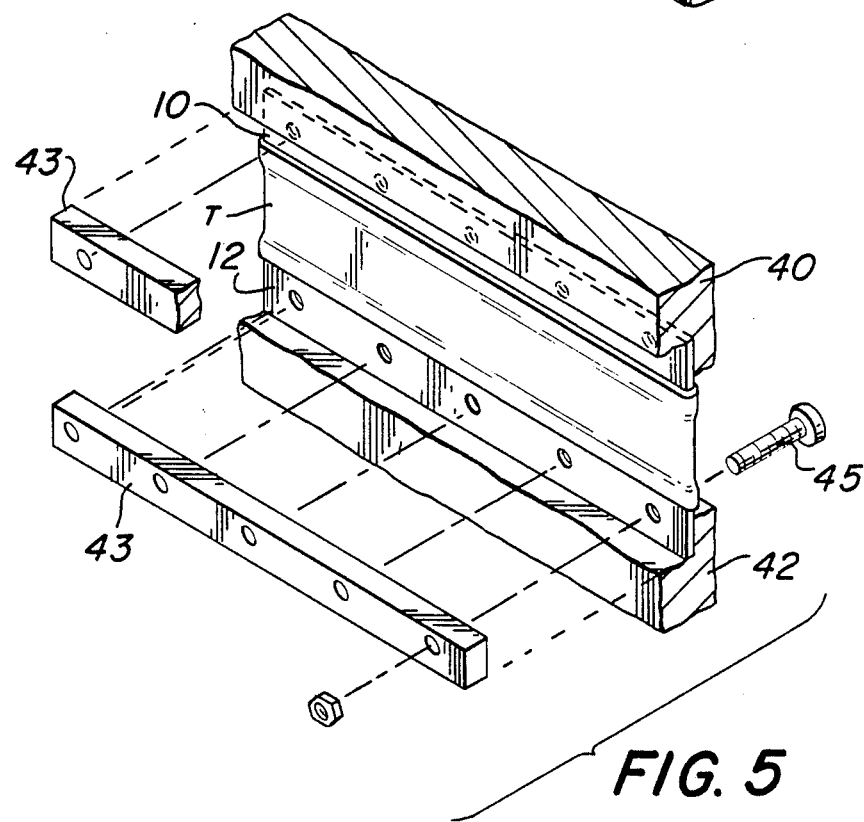
FIG. 5 is a fragmenting exploded view of the specimen and associated attachment of the testing machine of FIG. 1.

As shown in FIG. 5, the upper and lower fixtures 10 and 12, attached to the specimen T as described above, are fixed respectively to a loadsensing crosshead 40 and a movable crosshead 42 with clamps 43 and fasteners 45 through the holes 14. Crosshead 42 is securely mounted on the platform 30 for movement therewith while crosshead 40 is pivotally connected to load cells 44 at points coinciding with the ends of specimen T for measuring, in two vertical components $F_1$ and $F_2$, the total force exerted on the specimen by the actuator 26. The cells 44 are pivotally fixed to and extend down from the upper beam 20.

Since the load cells 44 deflect under load, and the loads in the two cells are not equal, they will deflect different amounts. If they were rigidly fixed to the crosshead 40, they would be subject to bending as well as tension. As illustrated in FIG. 7, this is prevented by pivotal connections at the cells. To this end, and eyebolts 46a and 46b are threadingly engaged in each load cell 44 and extend into recesses 47a and 47b in the crosshead 40 and boss 49 fixed to upper beam 20. Pins 48 extending horizontally through crosshead 40 and boss 49 on axes coinciding with respective ends of specimen T pivotally engage the openings in the eyebolts 46a and 46b.

Figure 8:
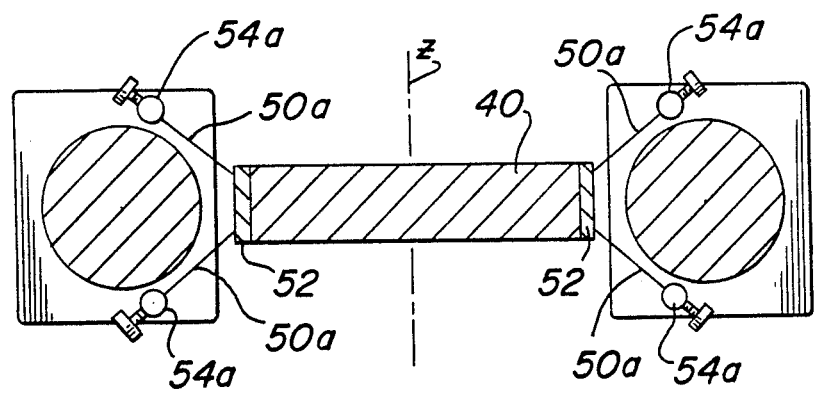
FIG. 8 is a cross sectional plan view of a portion of the testing machine taken along the line 8—8 of FIG. 1.
Figure 9:
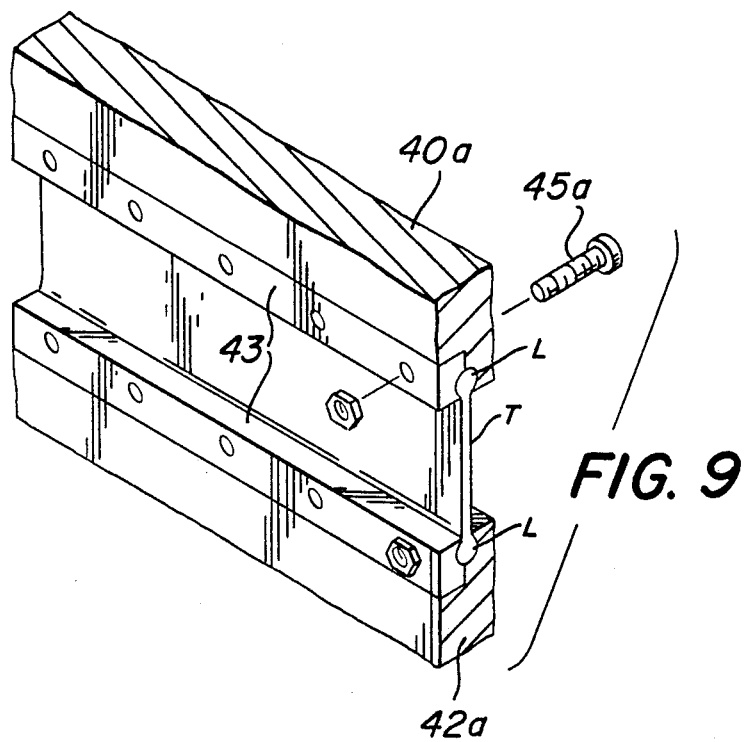
FIG. 9 is an isometric view of an alternate embodiment for the test specimen and associate components of the testing machine.

The pivotal connection, however, would still allow unwanted degrees of freedom in the crosshead 40 but for a stabilizing mechanism which is provided to lock out those motions which would significantly affect the force measurements at the load cells 44. As illustrated in FIGS. 1 and 8, two tiers of small steel cables, four in each tier, restrain the motions. The lower tier cables 50b are connected to the lower ends of brackets 52 which extend vertically from the ends of the crosshead 40. The cables extend laterally from either side of crosshead 40 at 45°0 to respective ferrules 54b, mounted beneath two collars 56 which, in turn, are each fixed to the columns 18. Similarly, the upper tier cables 50a connect to the upper ends of brackets 52, and extend at 45° laterally to ferrules 54a mounted above collars 56. The left and right pairs of cables 50a and 50b each stabilize a point in the plane of the cables, thereby locking out four degrees of freedom: lateral translation, fore and aft translation, yaw about the vertical y-axis, and pitch about the horizontal x-axis. Vertical motion and roll about the front-to-back z-axis are unimpeded, allowing independent measurement of the two forces $F_1$ and $F_2$ at load cells 44. FIG. 9 is an alternate embodiment for the test speciment T. The specimen is molded with a lip L on the longitudinal edges for gripping by recesses in crossheads 40a and 42a and clamps 43a when compressed by fasteners 45a.

The above-described method of determining crack length and growth measurements and operation of the testing machine will now be described. The elastomeric test speciment T is molded into an elongate configuration with substantially high length-to-width and width-to-thickness ratios and of a size suitable for the machine's capacity. Rigid fixtures 10 and 12 are then contiguously fixed to the long edges of the specimen and attached to the crossheads 40 and 42 of the machine. To induce crack growth in the specimen, a small cut is made in the vertical edge at one end. The actuator 26 is then energized to reciprocate the crosshead 42 and stretch cyclically the specimen crosswise at a preselected frequency and amplitude. The forces $F_1$ and $F_2$ sensed by load cells 44 are then observed and their values utilized to calculate the length and rate of any crack growth over a given period of time resulting from the stretching.

Some of the many advantages and novel features of the invention should now be readily apparent. For example, a testing method and apparatus is provided which enables an elastomeric test specimen to be subjected to pure shear strain in order to acquire the dynamic force data necessary to determine the length and growth of a crack. The method lends itself to automatic operation with high accuracy and efficiency, and is particularly suitable for practicing with the novel and improved testing machine of the invention.

While preferred method and apparatus for practicing the invention have been described in detail, various modifications, alterations and changes may be made without departing from the spirit and scope of the present invention as defined in the appended claims.

What is claimed is:

1. A method for testing an elongate elastomeric specimen of a preselected length, comprising the steps of:
   fixing the long edges of the specimen contiguous to parallel rigid members;
   fixing one of the members at two points adjacent the respective ends of the specimen;
   inducing a crack in the specimen;
   stretching the specimen with a tensile force applied to the other of the members, the stretching force being uniformly distributed along the length of the uncracked portion of the specimen;
   measuring the respective tensile forces at said points; and
   computing the crack length as a function of the specimen length and the measured forces.

2. A method according to claim 1, wherein said inducing step includes cutting the edge of one end of the specimen sharply to a depth sufficient to initiate cracking without further intervention.

3. A method according to claim 1, wherein said computing step includes calculating the crack length according to the following relationship:

$$c = \frac{F_2 - F_1}{F_2 + F_1} L$$

where c = crack length
L = specimen length
$F_1$, $F_2$ = tensile force at said points.

4. A method according to claim 1, wherein said tensile force is applied cyclically and for a preselected time period.

5. A method for testing an elastomer, comprising the steps of:
   preparing an elongate elastomeric specimen of a preselected length;
   fixing the long edges of the specimen contiguous to parallel rigid members;
   fixing one of the members at two points coinciding with the respective ends of the specimen;
   stretching the specimen with a cyclical tensile force applied to the other of the members for a preselected time period, the stretching force being uniformly distributed along the length of the uncracked portion of the specimen;
   measuring the respective tensile forces at said points; and
   computing the crack growth rate as a function of the specimen length, the measured forces and the time period.

6. A method according to claim 5, wherein said specimen has length-to-width and width-to-thickness ratios of about ten.

7. A method according to claim 5, wherein said inducing step includes cutting the edge of one end of the specimen with a sharp blade sufficient to initiate cracking without further intervention.

8. Apparatus for testing a thin elongate elastomeric specimen of preselected length and having an induced crack at the edge of one end, comprising, in combination:
   first means including fixtures formed to be contiguously secured to respective ones of the opposed longitudinal edges of the specimen along the entire length thereof; second means operatively connected to said first means for stretching the specimen crosswise; and third means operatively connected to one of said fixtures for measuring the stretching forces at two points coinciding with the ends of the specimen.

9. Apparatus for testing a thin elongate elastomeric specimen of preselected length and having an induced crack at the edge of one end, comprising, in combination:
   first means formed to secure the long edges of the specimen;
   second means operatively connected to said first means for stretching the specimen crosswise;

third means operatively connected to said first means for measuring the stretching forces at two points adjacent to the ends of the specimen; and stabilizing means operatively connected to said first means for restraining lateral translation in a plane normal to the direction of the stretching and rotation about any axis in said plane.

10. Apparatus for testing a thin elongate elastomeric specimen of preselected length and having an induced crack at the edge of one end, comprising, in combination:

first means formed to secure the long edges of the specimen, said first means includes fixtures formed to be contiguously secured to respective ones of the opposed long edges of the specimen;

second means operatively connected to said first means for stretching the specimen crosswise, said second means includes a support structure, an actuator operatively connected between said structure and one of said fixtures; and third means operatively connected to said first means for measuring the stretching forces at two points adjacent to the ends of the specimen, said third means includes load cells operatively connected between said structure and the other of said fixtures.

11. Apparatus according to claim 10, wherein said stabilizing means includes flexible braces, each attached to said fixtures adjacent to the ends of the specimen and extending laterally and attached to said support structure for preventing translation in the plane normal to the direction of the stretching and rotation about any axis in said plane.

12. Apparatus for testing a thin elongate elastomeric specimen of preselected length and having an induced crack at the edge of one end, comprising, in combination:

first means formed to secure the long edges of the specimen;

second means operatively connected to said first means for stretching the specimen crosswise; and third means operatively connected to said first means for measuring the stretching forces at two points adjacent to the ends of the specimen, said third means further includes a member pivotally connected to said first means for providing pivotal motion in the plane of the specimen.

13. Apparatus for testing a thin elongate elastomeric specimen of preselected length, and having an induced crack at the edge of one end, comprising, in combination:

first and second means formed to be contiguously secured to the respective long edges of the specimen;

support means;

actuator means connected between said support means and said second means for cyclically stretching the specimen crosswise;

sensor means connected between said support means and said first means for measuring the tensile forces at two points coinciding with the ends of the specimen;

whereby the growth rate of the induced crack can be determined as a function of the specimen length and the measured forces.

14. Apparatus according to claim 13, further comprising:

stabilizing means connected between said first means and said support means for restraining translation of said first means in a plane normal to the direction of the stretching and rotation about any axis in said plane.

15. Apparatus according to claim 13, wherein said sensor means includes load cells pivotally connected between said support means and said first means for providing rotation in the plane of the specimen.

16. Apparatus according to claim 13, wherein said support means includes a pair of columns separated by upper and middle beams and a base, said sensor means being connected to said upper beam and said actuator means being connected to said lower beam.

17. Apparatus according to claim 13, wherein said actuator means includes a servo system for selectively regulating the frequency and amplitude of the cyclical stretching.

* * * * *